United States Patent [19]
Dervieux et al.

[11] Patent Number: 5,175,142
[45] Date of Patent: Dec. 29, 1992

[54] COMPOSITIONS FOR SCENTING FINISHED ELASTOMERIC BASE PRODUCTS AS WELL AS THEIR SCENTING PROCESSES

[76] Inventors: Dominique Dervieux, Villa Artémise-2ter av. Henri Barbusse, 06100 Nice; Gerard Nouri, 20 Allee du Parc des Couvents, 57158 Montigny Les Metz; Jacky Munger, 3 rue du Haut Poirier, 57000 Metz, all of France

[21] Appl. No.: 281,455

[22] Filed: Dec. 8, 1988

[30] Foreign Application Priority Data

Dec. 8, 1987 [FR] France .................. 87 17204

[51] Int. Cl.⁵ .................. A61K 7/46; C11D 3/50
[52] U.S. Cl. .................. 512/4; 220/378; 252/90; 426/89; 426/96; 426/602; 512/5; 206/221; 206/69
[58] Field of Search .......... 512/5, 4; 220/20, 378; 426/89, 96, 602

[56] References Cited

U.S. PATENT DOCUMENTS

| | | | |
|---|---|---|---|
| 3,819,838 | 6/1974 | Smith et al. ............... | 512/4 |
| 3,906,116 | 9/1975 | Quesnel et al. ........... | 512/4 |
| 4,269,729 | 5/1981 | Maruyama et al. ....... | 512/4 |
| 4,276,312 | 6/1981 | Merritt ..................... | 512/4 |
| 4,576,737 | 3/1986 | Johnson .................... | 512/4 |
| 4,678,684 | 7/1987 | Sand ......................... | 427/213.36 |
| 4,720,417 | 1/1988 | Sweeny et al. ............ | 428/201 |
| 4,803,195 | 2/1989 | Holzner .................... | 512/4 |
| 4,842,761 | 6/1989 | Rutherford ................ | 512/4 |

FOREIGN PATENT DOCUMENTS

| | | | |
|---|---|---|---|
| 3415156 | 10/1985 | Fed. Rep. of Germany | 512/4 |
| 0111200 | 9/1978 | Japan ........................ | 512/4 |
| 0115762 | 10/1978 | Japan ........................ | 512/4 |
| 1327761 | 8/1973 | United Kingdom ....... | 512/4 |

*Primary Examiner*—Werren B. Lone
*Attorney, Agent, or Firm*—Young & Thompson

[57] ABSTRACT

A solid or liquid composition of food quality, non-allergenic and non-toxic, for scenting finished products formed of elastomers by contact of these finished products and these compositions before use. This chemically or physically isolated composition contains, in addition to one or several natural or artificial scents, one or several additives belonging to the group of agents for sugaring, sweetening, taste reinforcing, absorbing, coloring, lubricating, emulsifying, stabilizing, thickening, gelling, absorbing, anti-lumping, food preserving, antioxidation, and may be sterilized in different ways such as exposure to rays ($\beta$ type or the like). The invention is particularly useful for contraceptives, and comprises a package in which the contraceptive is contained isolated from a quantity of a scenting composition by means of a rupturable separator. Upon rupturing the separator, the product may be scented by massaging the package before opening it.

12 Claims, 5 Drawing Sheets

COMPOSITIONS FOR SCENTING FINISHED ELASTOMERIC BASE PRODUCTS AS WELL AS THEIR SCENTING PROCESSES

The present invention has for its object compositions for scenting finished elastomeric based products and relates to processes for scenting such finished products by contact with this composition as well as to packages containing the finished products adapted to be scented by this composition just before use. By finished elastomeric products, is meant products such as nursing bottle nipples, prophylactics, etc.

It has been attempted in the past to scent elastomeric products and these attempts practiced on the primary material, generally latex, have consisted in introducing scenting compounds or aromas into the mass of the elastomers, which is to say scenting the primary material prior to forming said products or by placing them in direct contact with non-isolated scents. The drawback of these methods is that they reduce the strength of the elastomers and therefore risk breaking especially if the product is thin; this risk is accordingly higher for prophylactics and leads to known difficulties.

It should also be noted that other solutions have consisted in placing scents in direct contact with the elastomers, but this has resulted in the scented products aging badly especially when they are in direct contact with elastomers in the presence of moisture and in packaging containing air.

The state of the art may be defined by the following patents:

DE-A-2 037 947: this patent relates to encapsulated products adapted to be used for cooking.

U.S. Pat. No. 3,819,838: this patent relates to an encapsulated composition and particularly a composition containing encapsulated scents in a solid material.

U.S. Pat. No. 4,276,312: this patent relates to materials containing an encapsulated product, in the form of particles or small rods easily dispersible in water.

U.S. Pat. No. 3,906,166: this patent relates to concentrated oleoresin-base emulsions and more particularly their encapsulation in a material.

EP-A-0 70 719: this patent relates to a process of encapsulation of volatile liquid and relates to compositions containing perfumes in encapsulated scents.

In fact, none of these documents has for its object the particular use according to the invention.

The present invention permits overcoming the drawbacks of the known processes of scenting these elastomers.

The present invention has for its object a process of scenting a finished product formed of elastomer characterized in that it consists in placing in contact with said product a solid or liquid composition of alimentary quality, non-allergenic and non-toxic, chemically or physically isolated from direct contact with said composition, also one or several natural or artificial scents containing one or several additives belonging to the group consisting of agents for micro-encapsulation, sugaring, sweetening, taste enhancing, absorbing, coloring, lubricating, emulsifying, stabilizing, thickening, gelling, absorbing, anti-lumping, food preserving, antioxidizing.

The invention relates to scenting compositions having no tendency to denature the elastomers and preserving their physical properties even over a long term and at temperatures varying over a wide range. Moreover, these compositions have "food" properties, which is to say that they are neither toxic nor allergenic neither for the mucosa and the digestive tract, nor for the skin; they can be sterilized, for example by irradiation ($\beta$ or the like) and packaged in containers or sealed evacuated packages.

The present invention has for an object, as a new industrial product, a solid or liquid food quality composition, non-allergenic and non-toxic, for scenting finished products made of elastomers, characterized in that it contains, in addition to one or several natural or artificial scents, one or several additives belonging to the group of agents for sugaring, sweetening, taste enhancing, absorbing, coloring, lubricating, emulsifying, stabilizing, thickening, gelling, absorbing, anti-lumping, food preserving, antioxidizing and others and that they can be sterilized, for example by irradiation ($\beta$ type or the like) and/or placed in evacuated packages.

According to an embodiment of the invention, the composition is solid and in addition to one or several natural or artificial scents, contains at least one of the preceding additives.

According to another embodiment of the invention, the composition is solid and contains more than 0 to nearly 100% of one or several natural or artificial scents, 0 to 50% of anti-lumping agent, 0 to nearly 100% of sugaring or sweetening agent, 0 to 20% of taste enhancement agents, 0 to 20% of coloring agent, 0 to 30% of food preservatives, 0 to 8% anti-oxidizing agent.

According to still another embodiment of the invention, the composition is solid and the natural or artificial scents of the recited compositions are micro-encapsulated by atomization in a material such as malto-dextrin, gum arabic, gum acacia, converted corn starch.

Preferably, said encapsulation material consists of gum arabic or gum acacia.

This micro-encapsulation permits isolation of the scents and, consequently, improves stability of the elastomers.

According to an embodiment of the invention, the anti-lumping agent is a food desiccator of the type of magnesium carbonate, silica, colloidal silica, iron silicates or their derivatives.

According to another embodiment of the invention, the composition is liquid and is comprised of an emulsion or an aqueous or alcoholic solution of natural or artificial scents of food quality. The scents may be entirely natural or alcoholic extracts.

According to another embodiment of the invention, the sugaring agent is a natural or synthetic sugar such as cerulose, glucose, lactose, saccharose, preferably a natural sugar extract of sugar cane or beetroot, or a sweetener for example synthetic sweeteners such as saccharine, aspartam, sorbitol, etc. or natural sweeteners such as licorice root extract, etc., or a mixture of sugaring agents.

According to an embodiment of the invention, relating particularly to liquid compositions, at least one of the additives is preferably an additive belonging to the group of alginates, pectins, carraghenates, gums, gelatins, glycerin and derivatives, converted starches.

According to another embodiment of the invention, the composition is liquid and contains 0 to almost 100% of one or several natural or artificial scents, 0 to almost 100% of emulsifying agent, 0 to almost 100% of sugaring or sweetening agent, 0 to 20% of taste enhancement agents, 0 to 20% of coloring agent, 0 to 30% of food preservatives, 0 to 8% (preferably 0.01%) of anti-oxidant, the balance being constituted by water or a hydroalcoholic solution of 30° De (degree Celsius) and of food quality. Preferably, the antioxidant is employed in a proportion of about 0.01%.

According to another embodiment of the invention, no matter what the scents or additives, at least one of the additives belongs to the group of comestible lubricants of a natural origin such as neutral oil which is a mixture of saturated fatty acid triglycerides of vegetable origin, preferably of medium chain length, or artificial origin, such as food oils or fats, etc. Preferably:

of natural origin, of low viscosity: spreading easily on the skin without leaving a glossy slick, without greatly staining the underwear, very stable at extreme ambient temperatures and at high humidity, with good solubility and miscibility in ethyl alcohol permitting fixing the essential oils and the other active ingredients which are volatile and sensitive to oxidization, of the type: citrus scents: lemon, orange, orange blossom, mandarin, etc. and mixtures, or aromatics: menthol, anise, etc. as needed in small proportions.

It is however necessary to avoid scents or additives which are phenols or their derivatives, oil-based antiseptics, fats derived from petroleum, gasoline, kerosene as well as organic products derived therefrom, which eliminates a large proportion of the artificial scents.

The advantage of the liquid solutions is that in addition to their lubricating action they can have a volatile nature and/or be completely absorbed by the skin or a mucous membrane.

According to another embodiment of the invention, said composition is formed of a mixture of a solid composition such as those which contain natural or artificial scents which can be micro-encapsulated by atomization of gum arabic or gum acacia or converted corn starch, etc., and a liquid or paste composition containing natural or artificial comestible lubricants, such as edible fats or oils, or the like.

The advantage of this mixture is the isolation of the scents in a comestible oil or fat in the form of pomade, cream, fluid emulsion, suspension, mixture.

The present invention also has for its object processes for scenting a finished product formed of elastomers consisting in placing said product in contact with the aforesaid composition after producing the finished product and, preferably, just before the use of said product, which is to say preparation when needed.

According to an embodiment of the process of the invention, the scenting of the finished product is achieved by placing the finished product and said solid or liquid composition in the same unitary package before sealing.

According to another embodiment of the process of the invention, the scenting of the finished product is achieved by placing the finished product and said composition in two distinct pockets separated by at least one wall of a unitary package before sealing. The wall can be broken by pressure or partially withdrawn just before use of said product.

Preferably, said composition is liquid.

The invention also has for an object a unitary sealed package containing the finished product of elastomer and the recited liquid or solid composition which is isolated from the finished product to be scented. Said composition is disposed in an evacuated pocket adapted to burst upon the application of external pressure, this pocket being therefore itself disposed in the envelope forming the packaging loosely or more or less fixedly.

According to another embodiment of the invention, the unitary sealed package comprises one or several more fragile intermediate walls adapted to be ruptured by pressure or partially withdrawn, the finished product of elastomer and said composition being each contained in one of two distinct pockets thus separated by at least one more fragile wall. This intermediate wall may itself be double and contain either the finished product or said composition, in the absence of air and be only partially sealed with the unitary package.

According to another embodiment, the fragile wall as recited separating the finished product and said composition is sealed only along a portion of one of the internal surfaces of one of the walls of the unitary package.

According to still another embodiment of the invention, the unitary sealed package comprises a single envelope in which are contained, separated by an isolating layer, the finished product of elastomer and a porous support impregnated with scents, the isolating layer being withdrawn just before use and the contact of the finished product and the porous support ensured by pressure. In this way, the liquid absorbed in the porous support is expelled and impregnates the finished product.

The choice of packaging materials, envelopes, separating walls, isolating means and supports of the foregoing embodiments will be effected according to different criteria:

the materials should be thermoweldable hermetically;

they should permit the sterilization of the contents particularly by irradiation ($\beta$ type or the like . . . );

they permit if desired evacuation of the air, either for the part containing the aromatic compound or both parts;

they will be opaque to light and of "food" quality, free from all toxicity and chemically compatible with the scents and additives;

certain walls or double walls may however be transparent or have transparent windows permitting checking the condition of the products and the absence of entry of the solid or liquid compound into the pocket in which the finished product is located if the latter is isolated from the compound.

The accompanying drawings are given by way of illustrative non-limiting examples. They show preferred embodiments according to the invention. They permit easy comprehension of the invention.

FIG. 1 is a plan view of an embodiment in which the package 1 is a single pocket, closed by thermowelding about its periphery 4, of two thermally-weldable sheets, which package contains the prophylactic 2 and scented liquid or powder 3.

FIG. 2 is a longitudinal cross sectional view of the package shown in FIG. 1.

FIG. 3 is a plan view of another embodiment in which the package 5 is formed by two pockets 6 and 7 separated by a thermoweld 8. Pocket 6 contains the prophylactic 10, the other pocket 7 contains the scented liquid 9. Pressure exerted in the direction of arrows F1 and F2 (FIG. 4) permits establishing contact between the scented liquid 9 and the prophylactic 10.

FIG. 4 is a cross sectional view of the embodiment of FIG. 3.

FIG. 5 is a plan view of another embodiment formed by two pockets 11 and 12. A pocket 11 contains the preservative 14 and the pocket 12 contains the scented liquid 13, this pocket 12 is easy to rupture under pressure.

FIG. 6 is a cross sectional view of the embodiment of FIG. 5.

FIG. 7 is a plan view in which the two pockets 17, 18 are closed by a medial separator 15 which separates the package 16.

FIG. 8 is a cross sectional view of the embodiment shown in FIG. 7.

FIG. 9 is a plan view of the package in which the hermetically sealed pocket 19 containing the scented composition 20 is secured by thermowelding to the internal surface 21 of the unitary package 22.

Figure 1:
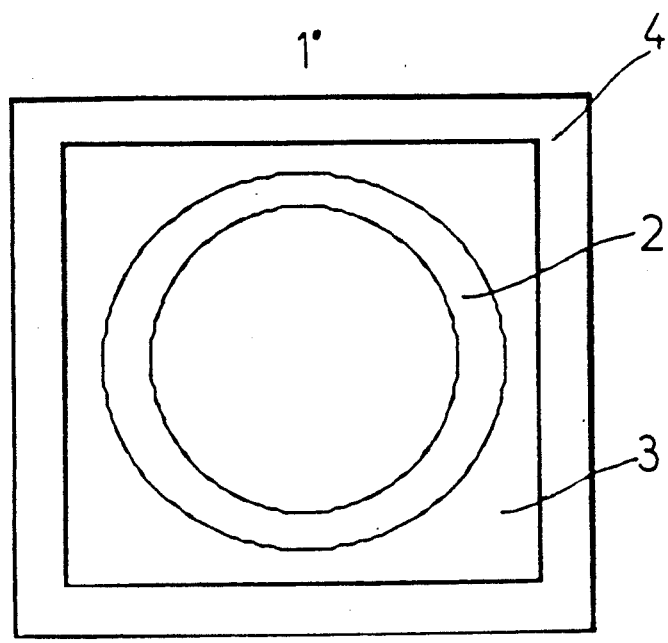
Figure 2:
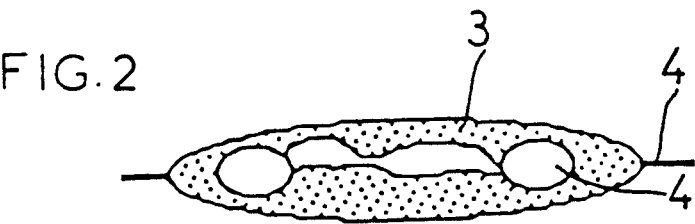
Figure 3:
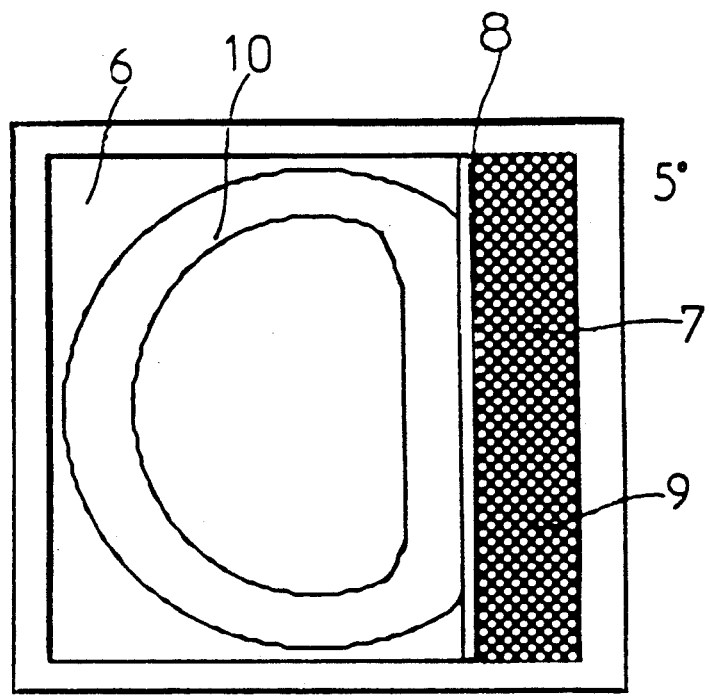
Figure 4:
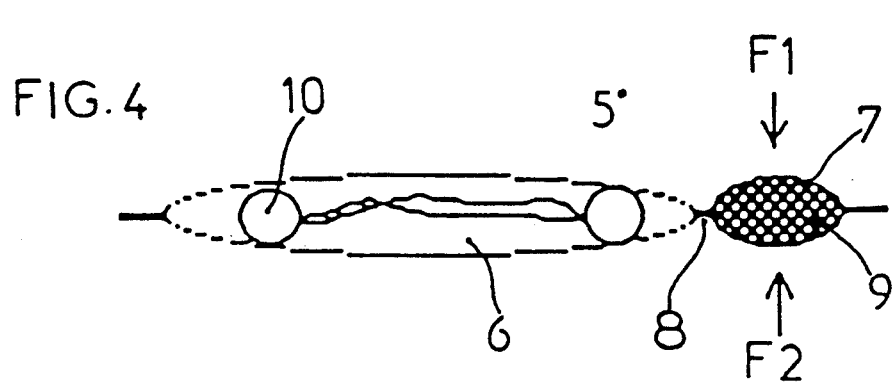
Figure 5:
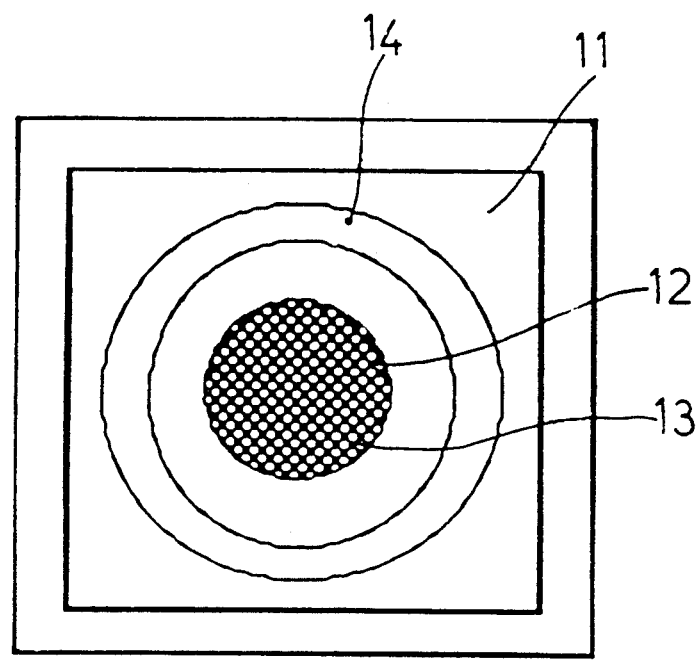
Figure 6:
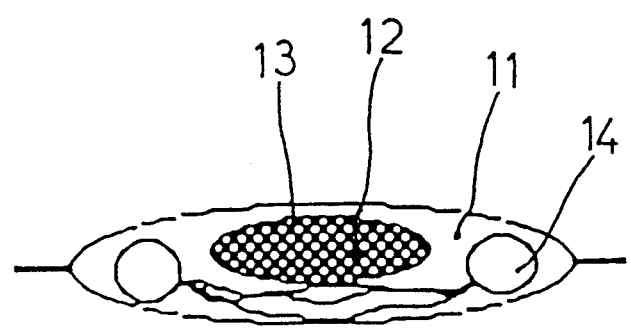
Figure 7:
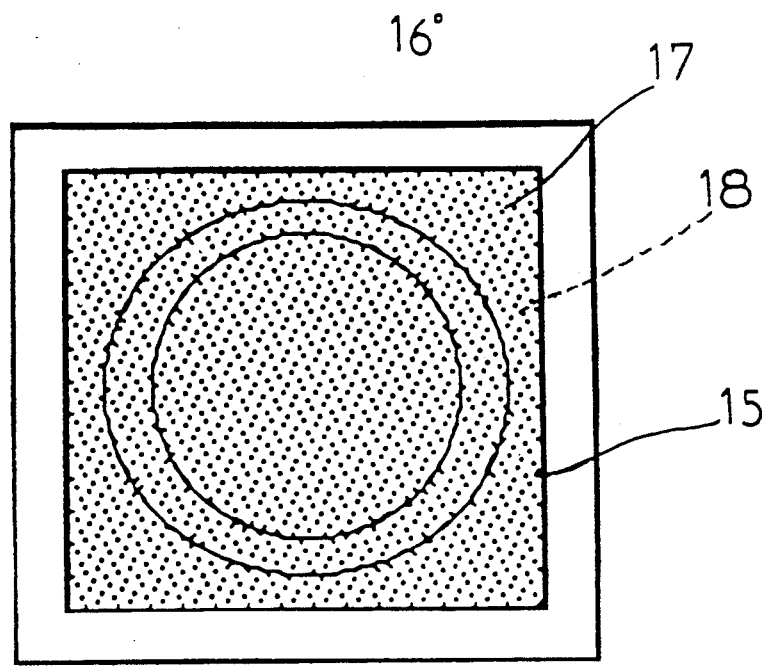
Figure 8:
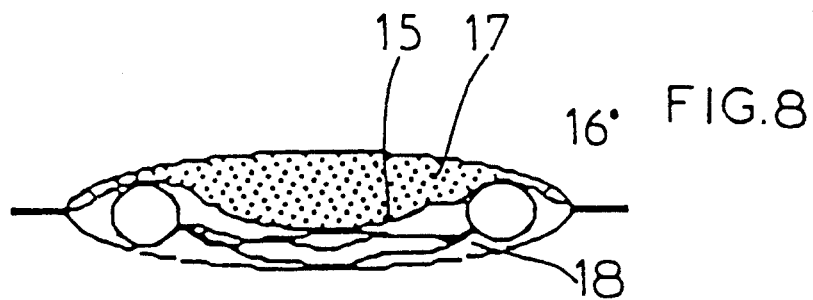
Figure 9:
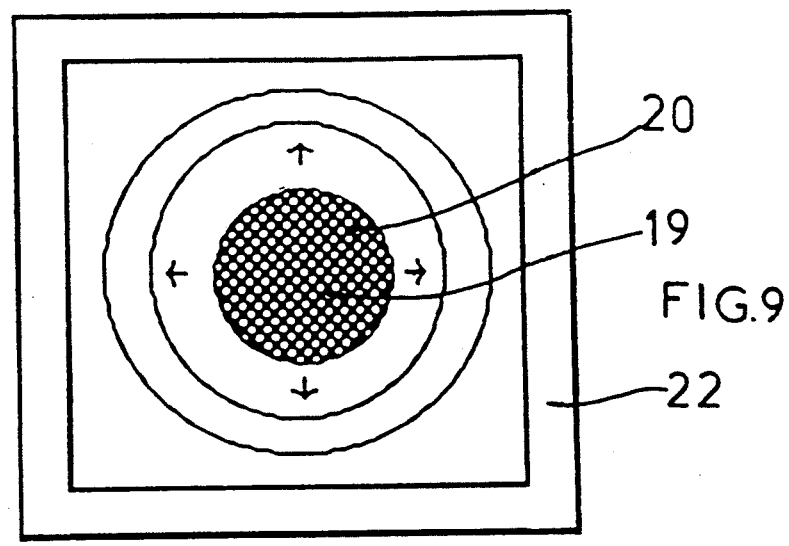
Figure 10:
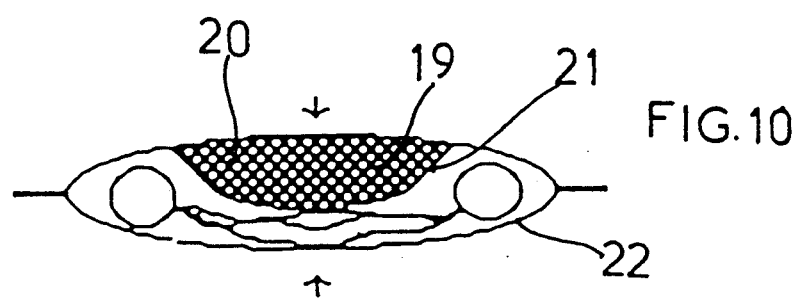
FIG. 10 is a cross sectional view of the embodiment shown in FIG. 9.
Figure 11:
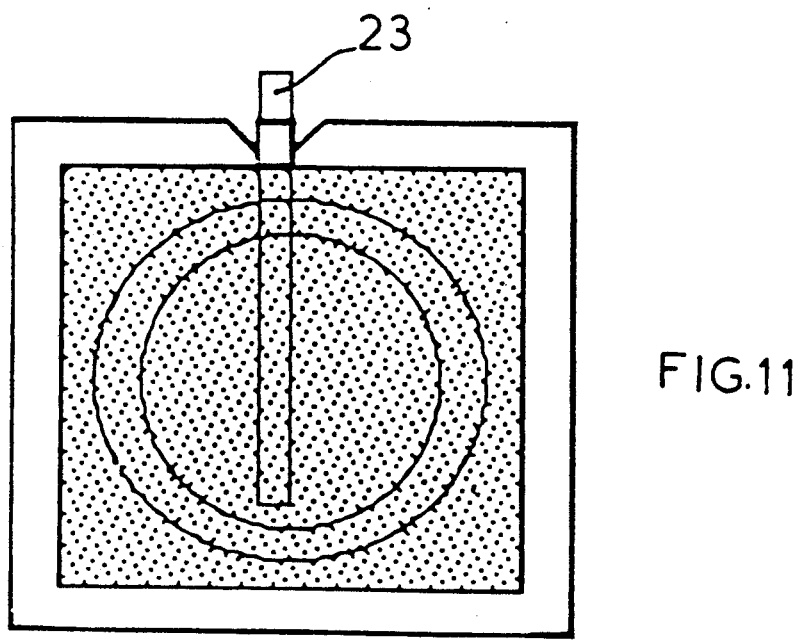
FIG. 11 is a plan view of an embodiment in which the medial separator is provided in the thermowelded pocket which can be torn off from the exterior. For this purpose, a pull tab 23 is provided to effect the tearing off of the internal separator.

Other objects and advantages of the invention will become apparent from a reading of the following description and from the non-limiting examples.

EXAMPLE 1

In a package comprising a single pocket closed by sealing so as to be subsequently irradiated by $\beta$ rays, there is placed a nursing bottle nipple of elastomer consisting of polybutadiene of food quality and a solid scenting composition comprised by:

90% natural scents micro-encapsulated in gum arabic;
10% "Aerosil".

It is to be noted that the direct contact of the composition with this nursing bottle nipple does not denature the elastomer of which it is formed or cause it to lose its physical qualities. Storage for 12 months at ambient temperature or for 7 days at 70° C. in an autoclave shows no denaturization or modification of the physical properties of the nipple.

EXAMPLE 2

Example 1 is repeated on a hevea latex prophylactic using however about 98% natural scents microencapsulated in gum acacia and 2% colloidal silica for anti-lumping. Results are obtained identical to those of Example 1.

EXAMPLE 3

In a package comprising a single pocket closed by sealing, about its periphery, there is disposed a nursing bottle nipple of elastomer consisting of polybutadiene of food quality and a liquid scenting composition comprised by:

20% of an aqueous solution of 40% natural scents consisting of fruit extract,
30% carraghenates of 15% moisture content, 49% water,
1% of preservatives.
sterilization by irradiation.

It is noted that the direct contact of the composition with this nipple does not denature the elastomer of which it is formed or cause it to lose its physical qualities. Storage for 12 months at ambient temperature or for 7 days at 70° C. in an autoclave shows no denaturization or modification of the physical qualities of the nipple.

EXAMPLE 4

In a package formed by a double envelope closed by sealing about its periphery, the wall between the two pockets being susceptible to be ruptured under pressure, there is introduced in one pocket a prophylactic formed of hevea elastomers and in the other pocket a liquid scenting composition comprised by:

99% food scents in 40% solution in water,
1% of a preservative consisting of sodium sorbate, the whole being irradiated with sterilizing rays.

When it is desired to use the prophylactic, there is exerted a pressure on the package to pierce the wall between the two pockets and promote contact between the liquid scenting composition and the prophylactic. The package is slightly massaged prior to its opening to ensure good contact between the prophylactic and the liquid composition.

EXAMPLE 5

In a package formed by an envelope closed by sealing about its periphery, the wall between the two pockets being adapted to be ruptured under pressure, there is introduced into one pocket a prophylactic of hevea latex and in the other pocket a liquid scenting composition comprised by:

88% water,
10% saccharose,
1% of artificial scent,
1% of preservative consisting of sodium sorbate sterilized by irradiation.

When it is desired to use the prophylactic, there is exerted a pressure on the package to pierce the wall between the two pockets and to promote contact between the scenting composition and the prophylactic. One presses on the liquid pocket and lightly massages the package prior to opening it to ensure good contact between the prophylactic and the solid composition.

EXAMPLE 6

Example 5 is repeated with the liquid composition replaced by a paste composition comprised by:

50% of natural scent micro-encapsulated in gum acacia,
0.01% of anti-oxidant,
q.s.p. 100 of a neutral oil of vegetable origin.

EXAMPLE 7

A porous support is impregnated with the same liquid composition as in Example 5. The support thus impregnated and an elastomeric nursing bottle nipple are placed in a single pocket closed by sealing about its periphery. Just before use, by pressure exerted on the package, the composition is expressed and saturates the nipple.

EXAMPLE 8

There is used a composition comprised by:
one part in a thousand of lemon oil,
q.s.p 100 of a neutral oil of vegetable origin: mixture of saturated fatty acid triglycerides, of vegetable origin and medium chain length, that is disposed in a pocket from which air has been evacuated and is adapted to be ruptured by pressure, this pocket and the prophylactic being disposed in a single envelope closed by sealing about its periphery. Pressure exerted on the envelope permits producing the bursting of the internal pocket and the consequent scenting of the prophylactic.

Of course, the present invention is not limited to the embodiments shown and described, but it is susceptible of numerous variations evident to one in the art without thereby departing from the spirit of the invention.

What is claimed is:

1. A process for superficially scenting a shaped product which comprises contacting said shaped product, just prior to its contemplated use, with a solid or liquid non-allergenic composition, non-toxic for humans and animals, wherein said composition is contained in an isolated pocket to be burst upon imposition of external pressure, and said contact just prior to said contemplated use is achieved by bursting open the said isolated pocket.

2. A unitary sealed package containing a food grade elastomeric shaped product and a liquid or viscous scenting composition in direct or indirect contact with said shaped product.

3. A unitary sealed package according to claim 2, wherein said composition is isolated from the shaped elastomeric product to be scented.

4. A unitary sealed package according to claim 2, which contains in a same pocket the shaped elastomeric product and said composition.

5. A unitary sealed package according to claim 2, which comprises said composition disposed in a pocket adapted to burst upon imposition of external pressure, said pocket itself being disposed in a pocket forming the package.

6. A unitary sealed package according to claim 2, which comprises two distinct pockets separated by a wall adapted to be ruptured by pressure or withdrawn at least partially, the shaped elastomeric product and said composition being each contained in a respective one of said pockets.

7. A unitary sealed package according to claim 2, which comprises a single pocket in which are contained, separated by an isolating layer, the shaped elastomeric product and a porous support impregnated with scents, the isolating layer being adapted to be ruptured or withdrawn at least partially, just before use, and the contact of the shaped elastomeric product and of the porous support being ensured by pressure such that the liquid absorbed in the porous support will be expelled and will saturate the shaped elastomeric product.

8. A unitary sealed package according to claim 5, wherein one or several walls or double walls are of a transparent material or comprise one or several transparent windows to permit verifying the preservation of the products and the absence of passage of the scented composition toward the pocket in which is disposed the shaped product.

9. A unitary sealed package according to claim 2, wherein the materials utilized for the package are hermetically thermoweldable, opaque to light, of food grade and are adapted for the sterilization of the contents.

10. A unitary sealed package according to claim 2, wherein the shaped product of elastomer is a prophylactic.

11. A unitary sealed package according to claim 2, wherein the composition contains 0 to almost 100% of at least one natural or artificial scent, 0 to 50% of anti-lumping agent, 0 to almost 100% of sugaring or sweetening agent, 0 to 20% of taste enhancing agent, 0 to 20% of coloring agent, 0 to 30% of food preservative, and 0 to 8% of anti-oxidizing agent.

12. A unitary sealed package according to claim 2, wherein the composition is liquid and contains 0 to almost 100% of at least one natural or artificial scent, 0 to almost 100% of emulsifying agent, 0 to almost 100% of sugaring or sweetening agent, 0 to 20% of taste reinforcing agent, 0 to 20% of coloring agent, 0 to 30% of food preservative, 0 to 8% of anti-oxidant agent, the balance being water or a hydro-alcoholic solution of 30° Bé and of food grade.

* * * * *